(12) United States Patent
Rudolf

(10) Patent No.: US 7,623,240 B2
(45) Date of Patent: Nov. 24, 2009

(54) OPTICAL MEASURING DEVICE FOR TEST STRIPS

(75) Inventor: Heiko Rudolf, Munich (DE)

(73) Assignee: Iris Deutschland GmbH, Marburg (DE)

( * ) Notice: Subject to any disclaimer, the term of this patent is extended or adjusted under 35 U.S.C. 154(b) by 149 days.

(21) Appl. No.: 10/496,356

(22) PCT Filed: Nov. 18, 2002

(86) PCT No.: PCT/US02/36885

§ 371 (c)(1),
(2), (4) Date: Mar. 6, 2006

(87) PCT Pub. No.: WO03/044474

PCT Pub. Date: May 30, 2003

(65) Prior Publication Data

US 2006/0176483 A1    Aug. 10, 2006

(30) Foreign Application Priority Data

Nov. 20, 2001   (DE) ............................... 101 56 804

(51) Int. Cl.
*G01J 3/46* (2006.01)
*G01N 33/48* (2006.01)
(52) U.S. Cl. ........................................ 356/402; 356/39
(58) Field of Classification Search ............. 356/39, 356/402, 429, 424
See application file for complete search history.

(56) References Cited

U.S. PATENT DOCUMENTS 3,910,701 A * 10/1975 Henderson et al. ............ 356/39
4,676,653 A * 6/1987 Strohmeier et al. ......... 356/446
5,143,694 A    9/1992 Schafer et al.
5,144,117 A    9/1992 Hasegawa et al.
5,477,326 A * 12/1995 Dosmann ................... 356/406
5,563,042 A * 10/1996 Phillips et al. ................. 435/14

(Continued)

FOREIGN PATENT DOCUMENTS

| JP | 01-204481 | 8/1989 |
| JP | 06-070633 B2 | 9/1994 |
| JP | 07-005110 | 10/1995 |
| JP | 2771309 B2 | 4/1998 |
| JP | 2001-141644 | 5/2001 |
| JP | 2001-183309 | 6/2001 |

OTHER PUBLICATIONS

English abstract of Japanese Patent No. 07-005110.

(Continued)

*Primary Examiner*—Roy Punnoose
(74) *Attorney, Agent, or Firm*—DLA Piper LLP (US)

(57) ABSTRACT

An optical measuring device (10) for detecting the coloring of test fields of a test strip (12), which is to be wetted with a liquid for detecting substances in said liquid, whereupon the reflectivity of the test fields changes depending on the concentrations of the substances to be detected, comprising: a measuring plane (14) wherein said test strip (12) is to be placed; an illumination device (16) for illuminating the measuring plane (14); a planar image sensor (36); an optical system for imaging said measuring plane (14) onto the image sensor (36); and an electronic evaluation unit (52) for evaluation of the signals detected by said image sensor (36), said illumination device (16) comprises light sources (18, 20, 22) or other means of different colors which serve to alternatively illuminate said measuring plane (14) in different colors, wherein said electronic evaluation unit (52) detects the coloring of the test fields from the images obtained under different color illuminations.

20 Claims, 5 Drawing Sheets

U.S. PATENT DOCUMENTS

| | | | | |
|---|---|---|---|---|
| 5,597,532 | A * | 1/1997 | Connolly | 422/58 |
| 5,995,236 | A * | 11/1999 | Roth et al. | 356/445 |
| 6,027,692 | A * | 2/2000 | Galen et al. | 422/82.05 |
| 6,201,607 | B1 * | 3/2001 | Roth et al. | 356/445 |
| 6,261,522 | B1 * | 7/2001 | Hough et al. | 422/82.05 |
| 6,639,669 | B2 * | 10/2003 | Hubble et al. | 356/319 |
| 2007/0086004 | A1 * | 4/2007 | Maier et al. | 356/301 |

OTHER PUBLICATIONS

JP Patent Office machine translation of Japanese Patent No. 07-005110.

English abstract of Japanese Patent No. 2001-183309.

JP Patent Office machine translation of Japanese Patent No. 2001-183309.

Abstract of JP Publication 2001-141644, Pub. Date May 25, 2001, printed from Patent Abstracts of Japan.

Abstract of JP Publication 01-204481, Pub. Date Aug. 17, 1989, printed from Patent Abstracts of Japan.

Abstract of JP Publication 03-186762, Pub Date Aug. 14, 1991 corresponding to JP Pub 06-070633 B2, Pub. Date Sep. 7, 1994, printed from Patent Abstracts of Japan.

Abstract of JP Publication 2771309 B2, Pub Date Jul. 02, 1998, corresponding to JP Patent 2771309 B2, Pub. Date Apr. 17, 1998, printed from esp@cenet database.

JP Patent Office machine translation of Japanese Patent Publication 2001-141644, Pub. Date May 25, 2001.

* cited by examiner

OPTICAL MEASURING DEVICE FOR TEST STRIPS

BACKGROUND OF THE INVENTION

The present invention concerns an optical measuring device for detecting the coloring of test fields of a test strip, which is wetted with a liquid for detecting substances in said liquid, whereupon the reflectivity of the test fields changes depending on the concentration of the substances to be detected, comprising
- a measuring plane wherein said test strip is to be placed,
- an illumination device for illuminating the measuring plane,
- a planar image sensor,
- an optical system for imaging said measuring plane onto the image sensor, and
- an electronic evaluation unit for evaluation of the signals detected by said image sensor.

Optical measuring devices of this kind are e.g. known as part of test strip analysis apparatus, which are used for examining urine or blood test strips in doctor's practices, hospitals or medical laboratories. The test strips to be analyzed often comprise a plurality of test fields, each of which serves to detect another substance. In such measuring devices, the test strip is illuminated as a whole and imaged onto the image sensor. From the image obtained, the electronic evaluation unit may then determine the coloring of all test fields across the test strip. Thus, it is not necessary to scan the individual test fields and the measurement of the test strip may be conducted in a shorter time, wherein the structure of the measuring device is simpler.

For detecting the coloring of a test field, its reflectivity for light of three different wavelengths has to be determined. In a conventional measuring device, the test strip is illuminated with white light and imaged onto an image sensor comprising sensor elements, each of which is sensitive to one of three wavelengths (colors). The light-sensitive elements are arranged in a planar matrix whose lines each comprise sensor elements sensitive to the light of the same color. Thus, there are three types of such color lines comprised in the image sensor, the order of adjacent color lines being such that one color line of the first type is followed by one of the second type and one of the second type is followed by one of the third type and one of the third type is followed by one of the first type.

Thus, three images are effectively detected by the image sensor sequentially, each time one of the entirety of color lines of one type, which represent the intensity of three spectral components of the same colored picture. From the intensity of the spectral components in every image point, basically a colored image may be calculated.

However, a problem is posed by the fact that these three images do not really represent the spectral components of the same image points since the color lines are offset from each other. If now these three images are taken for color evaluation, a systematic error occurs due to the finite width of the color lines.

SUMMARY OF THE INVENTION

Therefore, the present invention is to solve the problem of providing an optical measuring device of the above-mentioned kind, which avoids this systematic error. This problem is solved by an optical measuring device of the above kind in that the illumination device comprises light sources of different colors or other means that serve to alternatively illuminate the measuring plane with different colors and in that the electronic evaluation means detects the coloring of the test fields from the images obtained under different illumination.

Thus, the measuring device of the present invention does not require an image sensor having color lines but an image sensor whose light-sensitive elements detect the intensity of the light received independent from its wavelength. In the images obtained under different color illumination, the same image point (i.e. the signal received under different color illumination at the same sensor element) is generated by a light that has been reflected on the same point on the test strip. From the relative reflectivity of these points under different color illumination, the respective color may be calculated without any systematic errors occurring.

In a preferred embodiment, the image sensor comprises light-sensitive CMOS components arranged in a planar matrix.

Preferably, the illumination unit uses colored LEDs as light sources. In a preferred embodiment, the light sources comprise blue, green and orange LEDs, in particular LEDs having wavelengths of 450 nm, 530 nm and 620 nm.

In order to uniformly illuminate a test strip in a measuring plane, it is advantageous to arrange the light sources in a series on a transmitter board. It is especially advantageous if the arrangement density of light sources on the transmitter board increases within the series from the center in an outward direction. Due to such inhomogeneous distribution of light sources on the transmitter board, the test strip may be almost homogeneously illuminated in the measuring plane.

In a further preferred embodiment, on both sides of the series of light sources in parallel to the longitudinal direction of the series, screens are employed which focus the light emitted by the light sources on a strip-shaped portion in the measuring plane in which the test strip is to be placed. The screens preferably extend substantially over the length of the series of light sources and comprise a plurality of surface segments extending over the entire length of the transmitter board, wherein said surface segments' inclination angle relative to the transmitter board increases in correspondence with an increasing distance therefrom. With these screens, a test strip in the measuring plane may be illuminated with high intensity but nevertheless almost homogeneously.

The screens preferably consist of parts that have been milled or manufactured by injection molding, said parts having a reflecting layer or being laminated with a reflecting film. Thus, the screens are stable and can be manufactured at low cost.

As has been mentioned above, the color of a test field is detected by the relative reflectivity of the test field for light of three different wavelengths. If, for example, a test field is illuminated three times in a row with lights of different colors that, however, have different intensities, the relative reflectivity corresponds to the relation of intensities that are detected by the image sensor in the image of the test field. However, it is not indispensably necessary to permanently illuminate the test strip with light of the same intensity. What is important is that the intensity of illumination is known, thus, the relative reflectivity can be calculated from the measured intensities at the image sensor. Further, it may occur that the intensity of illumination changes in operation. If, e.g. colored LEDs are used for the illumination means, these are subject to wear which diminishes their performance.

For detecting a change of illumination intensity during operation it is advantageous to provide a first reference surface that is arranged such that it is illuminated by the illumination unit together with the test strip and imaged by the optical system onto the image sensor. By means of the image of this reference surface, the electronic evaluation unit may determine any illumination changes, such as a change in intensity of illumination with one of the colors as a whole or only within a portion of the measuring plane. In case such change is determined, it is necessary to newly calibrate the measuring device.

For calibration of the measuring device, the local intensity distribution on the measuring plane for all three colors has to be known. Preferably, the optical measuring device therefore has a second reference surface adjustable between a first position in which it takes the position of a test strip during measuring and a second position in which it cannot be imaged by the optical system onto the image sensor. The optical measuring device may thus calibrate itself by an adjustment of the second surface to the first position, an illumination subsequently with the different colors and by using the images provided by the evaluation unit as calibration standard. Such calibration procedure may for example routinely be carried out by the measuring device upon switching on the measuring device or after a predetermined amount of measurements has been made.

In an advantageous embodiment, the second reference surface is formed by a surface of a strip-shaped plate whose first end is equipped with a first arm at least almost perpendicular with respect to said second reference surface and pivotable about an axis parallel with respect to the reference surface. By adjusting the arm, the second reference surface can be adjusted between its first and second positions. Preferably, a second arm is further mounted to the second end of the strip-shaped plate, said arm being substantially parallel with the first arm and pivotable about the same axis as the first arm. The first arm is discharged by the second arm.

Preferably, a bar is pivotally supported with its first end by the first arm for adjusting the second reference surface between its first and its second position. In a preferred embodiment, this bar is mounted with its second end to a first lever pivotable about a first lever axis and biased into a first lever position by means of a biasing element, in which position the reference surface takes its second position and the lever is adjustable against the biasing force of the biasing element to a second lever position in which the reference surface takes its first position. Preferably, the first lever is actuated by means of an eccentric drive.

The device according to the invention may be used as part of a test strip analysis apparatus in which the test strips usually are advanced towards the measuring means by means of belts or the like. However, when measured, the test strip has to be in a static condition. This is most simply obtained when the conveying surface of the transport means of the test strip analysis apparatus lies in the measuring plane and the test strip is shortly kept in its measuring position on the conveying surface. In an advantageous embodiment, the optical measuring device therefore comprises a means for holding and aligning a test strip in its measuring position.

Preferably, these means are defined by two at least almost parallel pins movable along their longitudinal axis between a first position in which they protrude into said measuring plane and a second position in which they are entirely outside said measuring plane. In their first position, these pins protrude into the measuring plane so that a test strip conveyed in the measuring plane is caught at the pins and aligns relative to these pins in a measuring position. Preferably, the pins are biased into their second position and adjustable against the biasing force to their first position by a lever element. Preferably, the lever element is adjusted by the same eccentric drive as the first lever.

In a particularly preferred embodiment, the eccentric drive is formed by a rotating disc driven by a motor, on the surface of which a pin is arranged perpendicularly thereto such that upon rotation of the disc in its first rotational direction, said pin engagingly moves said first lever into its second lever position and that upon rotation of the disc in its second rotational direction, said pin engagingly moves said lever element such that said lever element moves said pins into their first position.

Even though, the optical measuring device according to the invention makes use of an illumination means that is able to alternatively illuminate the measuring plane with different colors, all of the features concerning the arrangement of the light sources, the screens, the first and second reference surfaces, the adjustment mechanism of the second reference surface and the means for holding and aligning a test strip in its measuring position may also be advantageously used with conventional measuring means, in which white light for illuminating and filters, i.e. image sensors having color lines are used.

BRIEF DESCRIPTION OF THE DRAWING

Further advantages and features of the solution according to the invention will become apparent from the following description which outlines the invention by means of an embodiment with reference to the accompanying drawings, wherein.

DETAILED DESCRIPTION OF THE INVENTION

Figure 1:
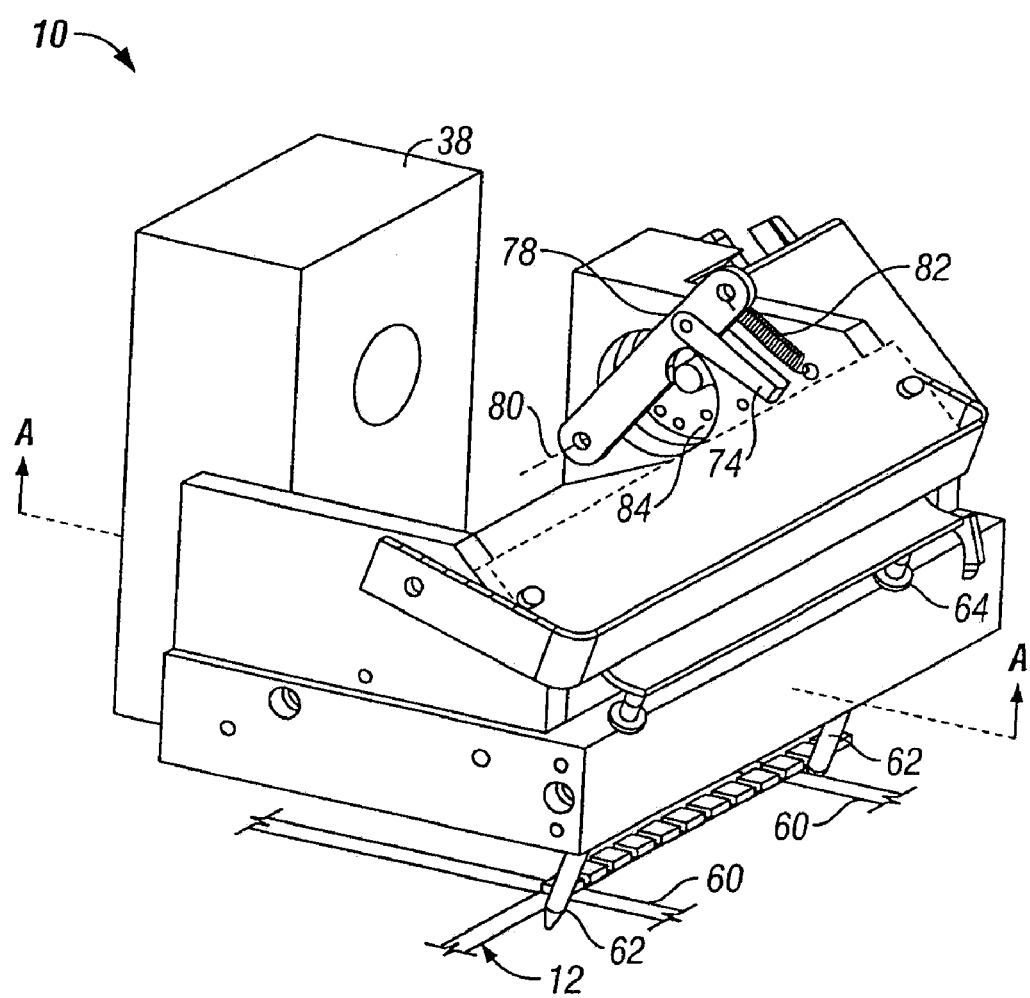
FIG. 1 is a perspective view of the optical measuring means according to the invention.

FIG. 1 illustrates a perspective view of the optical measuring device 10 according to the invention, in which a test strip 12 extends in the measuring plane 14 (cf. FIG. 2) in its measuring position.

Figure 2:
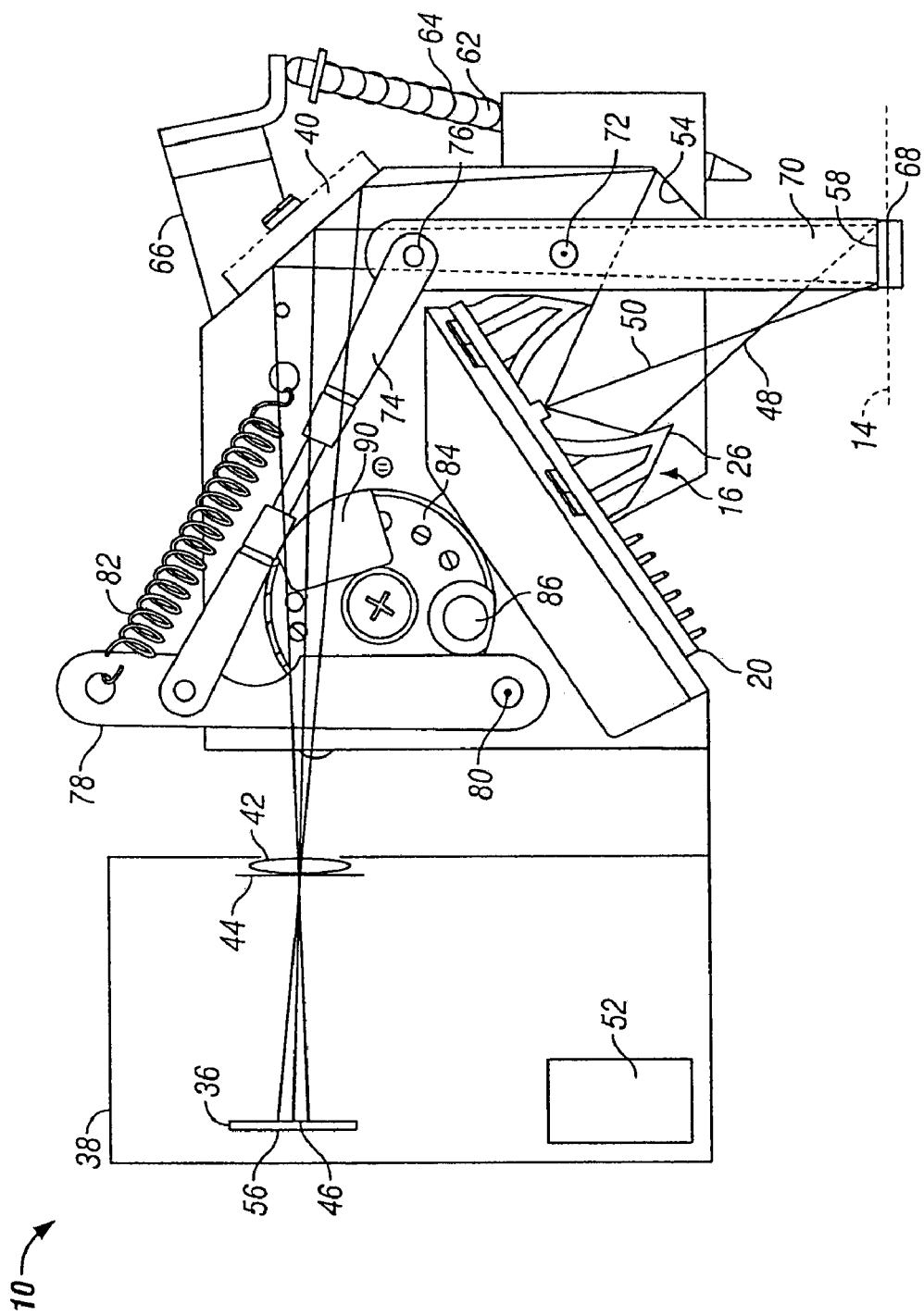
FIG. 2 is a cross-section through a portion of the optical measuring device along A-A' in FIG. 1.
Figure 5:
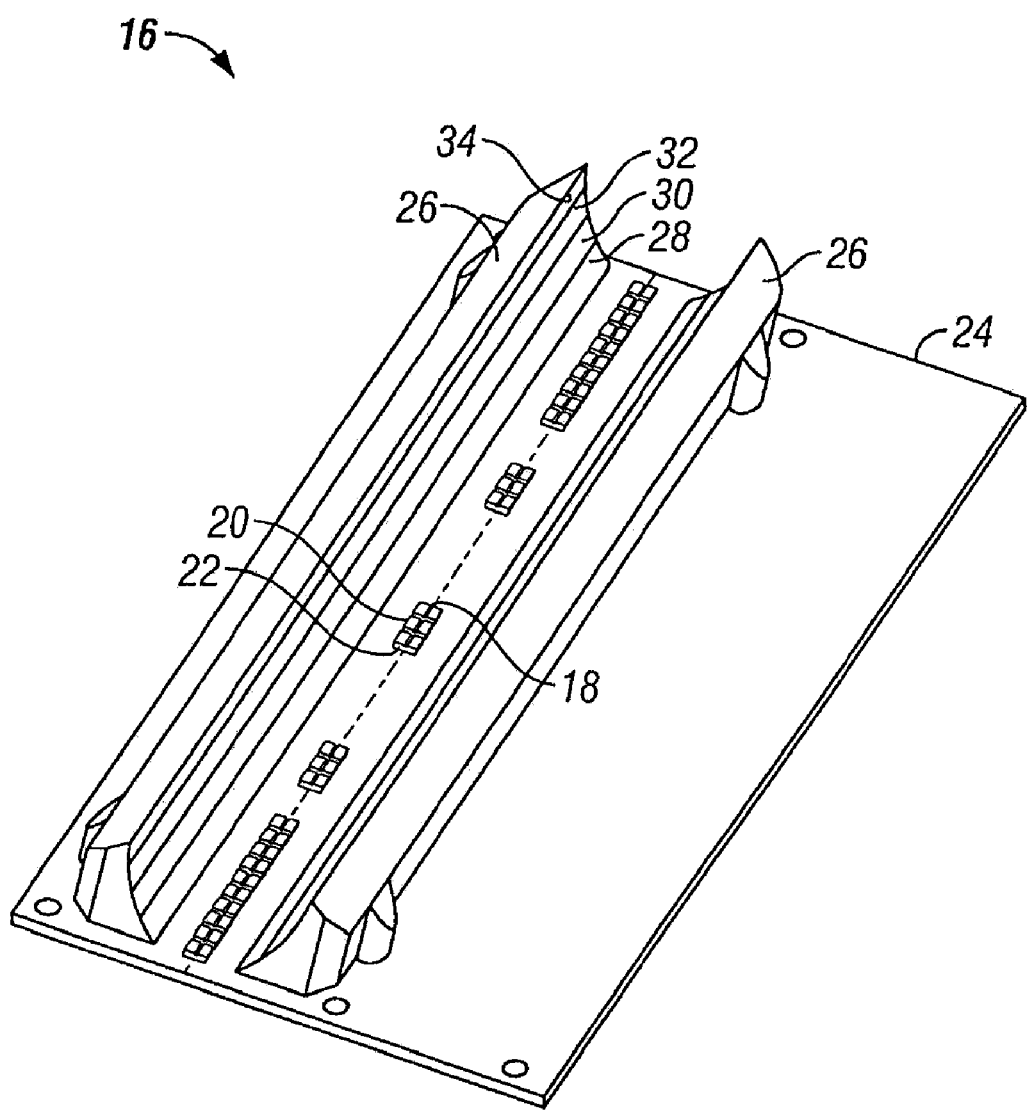
FIG. 5 is a perspective view of the illumination unit.

FIG. 2 shows a cross-section through the measuring device of FIG. 1 along A-A'. An illumination means 16 is illustrated by means of which a strip-shaped portion of the measuring plane, in which the test strip 12 is in its measuring position, may be illuminated with different colors. FIG. 5 shows a perspective view of the illumination means 16. The illumination means 16 comprise blue 18, green 20 and orange 22 LEDs having wavelengths of 450 nm, 530 nm and 620 nm in a serial order on a transmitter board 24. This serial arrangement of the LEDs is particularly suitable for illuminating the strip-shaped portion on the measuring plane 14. Within the series, blue 18, green 20 and orange LEDs 22 are respectively placed closely adjacent to one another in one group so that the measuring plane is uniformly illuminated in all three colors with the same intensity distribution. The groups of LEDs are arranged in a series such that their arrangement density of light sources on the transmitter board increases within the series from the center in an outward direction. This inhomogeneous arrangement of LEDs in a series results in an almost homogeneous illumination intensity on the measuring plane in the field of the test strip.

In parallel to the longitudinal direction of the LED series, screens 26 are disposed which focus the light emitted by the LEDs onto a strip-shaped portion, in which the test strip extends in its measuring position. The screens 26 extend over the entire length of the LED series. They comprise four surface segments 28, 30, 32 and 34, extending over the entire length of the screen 26. The inclination angle of the surface segments increases relative to the transmission board 24 in correspondence with an increasing distance therefrom. The screens 26 are made of parts having been manufactured by injection molding and whose surfaces 28, 30, 32 and 34 are provided with a reflecting layer.

The light emitted by the illumination unit 16 is diffusely reflected at the test strip 12 and the test strip is imaged via an optical system onto a planar image sensor 36, which is disposed in a housing 38 that is impermeable against light. The optical system comprises a mirror 40, a lens 42 and a screen 44. In FIG. 2 it is not the test strip 12 but the second reference surface 58 that is imaged onto the image sensor 36. Since the second reference surface 58, as will be described in more detail below, takes the position of a test strip during measuring, the position of the image 46 of the test strip is the same as the one of the image of the reference surface. In FIG. 2, the generation of the image 46 at the image sensor 36 is illustrated by means of two exemplary rays of light 48, 50. The optical path is folded at the mirror 40 thus maintaining the measuring device in its entirety compact.

The image sensor 36 comprises a plurality of light sensitive CMOS parts generating a signal depending on the intensity of the light illuminating them. The light sensitive elements are arranged in a planar matrix and each of them serves to generate an image point (pixel) of the image 46.

In the following, it shall be described how to detect the coloring of the test fields of the test strip 12 by means of the measuring device according to the invention. For this purpose, one of a plurality of light sensitive sensor elements is selected. Light is imaged onto the sensor element by the optical system, the light being diffusely reflected from a certain point, i.e. a very small portion, in one of the test fields. Thus, the sensor element detects the intensity of the light reflected at that point. If now this point is illuminated three times sequentially with blue, green and orange light having the same intensity, the relations of intensities measured at the sensor element represent the relative reflectivity for light of these three colors. Thus, however, the color of the test field is clearly determined. The signals generated at the image sensor 36 are transmitted to an evaluation unit 52 that detects the color of the original image, i.e. of the point or small portion on the test field, from these three signals generated upon a three-time illumination at each of the image points. Due to the plurality of light sensitive sensor elements which are comprised in the image sensor 36, the determination of color may be performed sequentially for a corresponding number of pixels in the test plane.

For determining the relative reflectivity it is certainly not necessary to illuminate each pixel in each color with light having the same intensity. What is important is that the evaluation unit 52 gains information about the relation of intensities of the different colors at one pixel in the measuring plane so that it may be taken into account when calculating the relative reflectivity. By resorting to this information, the measuring device may be calibrated according to the illumination conditions. However, the illumination of the measuring plane may vary in the course of time for a great number of reasons, e.g. due to the wear of the LEDs, defective LEDs or even only due to contaminations in the illumination means. As a consequence, the measuring device has to be calibrated anew.

For immediately determining during operation a change of intensity of illumination of the measuring plane, the measuring device 10 according to the invention is provided with a first reference surface 54, which is arranged such that it is illuminated by the illumination unit 16 together with the test strip and imaged by the optical system onto the image sensor 36. This first reference surface 54 is illustrated in FIG. 2 and its image on the image sensor 36 has been designated 56. As soon as there is a change of illumination, the image 56 changes on the image sensor 36, which in turn is detected by the evaluation unit 52. Then, the evaluation unit 52 causes the self-calibration of the measuring device.

However, for calibrating the measuring means, the image 56 of the first reference surface 54 cannot be resorted to since the illumination intensity distribution on the first reference surface 54 is not identical with the one in the measuring plane. Therefore, a second reference surface 58 is provided which is adjustable from a second position, in which it is not illuminated by the illumination means 16 and not imaged by the optical system onto the image sensor 36, to a first position, in which it takes the position of a test strip during measurement. The image of this second reference surface 58 serves to calibrate the measuring means.

Figure 4:
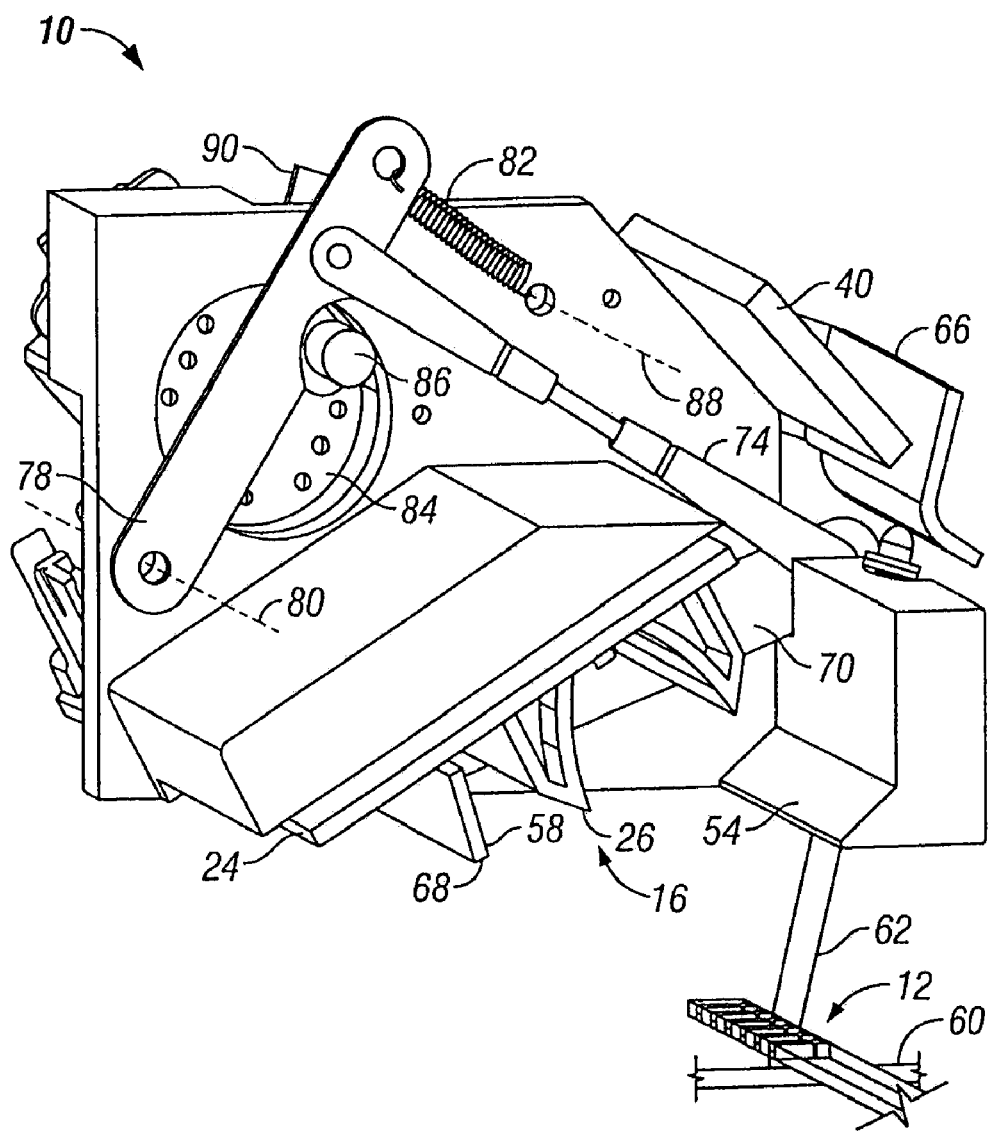

As shown in FIG. 1 and FIG. 4, the measuring device according to the invention may be used for a test strip analysis apparatus, in which the test strips are advanced towards the measuring device placed across transport belts 60. It is particularly advantageous to provide a construction in which the transport belts 60 form a conveying surface which coincides with the 35 measuring plane. Thus, the test strip 12 may be measured lying on the transport belt 60. However, this requires holding and aligning the test strip in its measuring position.

Figure 3:
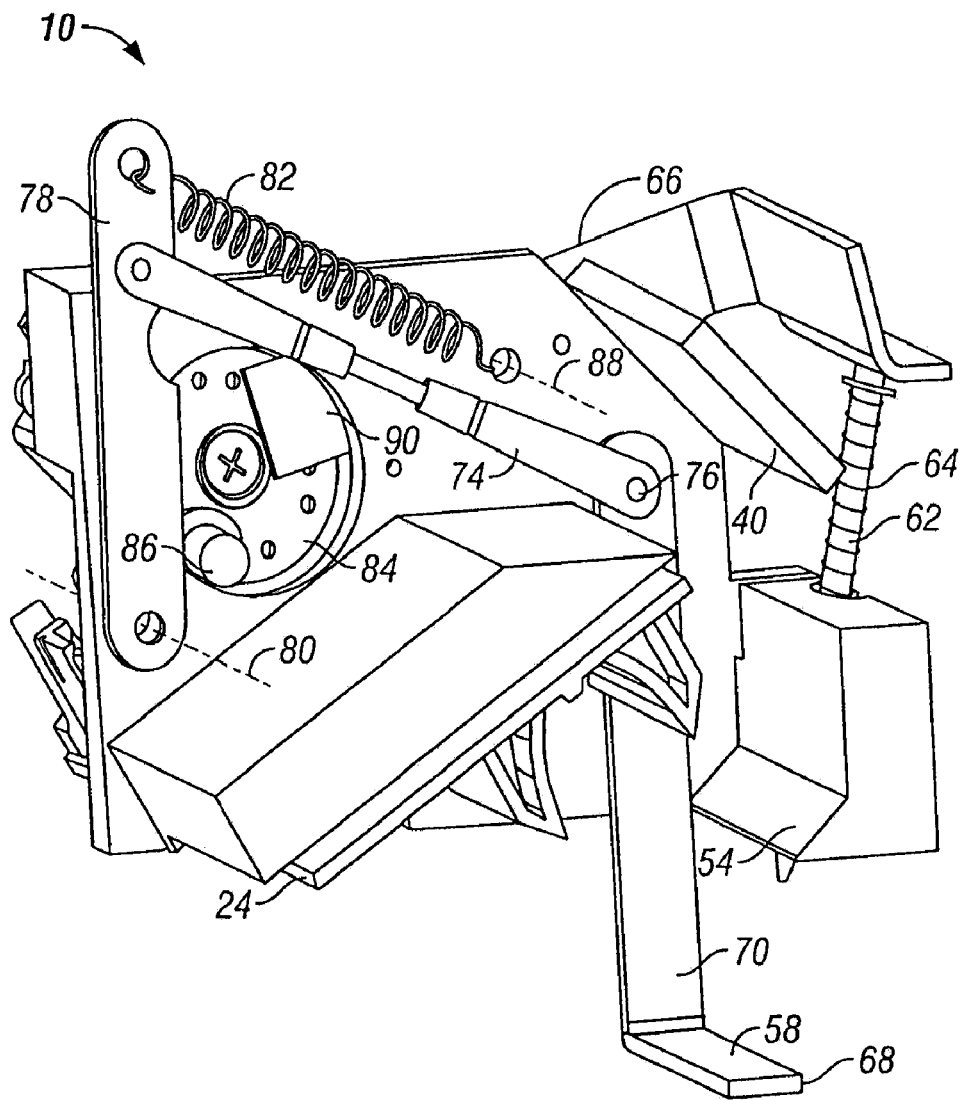
FIG. 3 is a perspective view of the section of FIG. 2 with the second reference surface in its first position, FIG. 4 corresponds with FIG. 3, wherein the second reference surface is in its second position and a test strip in its measuring position.

With regard to the illustrated measuring device two pins 62 are provided that are movable along their longitudinal axis between a first position in which they protrude into said measuring plane (cf. FIG. 1 and FIG. 4) and a second position in which they are entirely outside said measuring plane (cf. FIG. 2 and FIG. 3). The pins 62 are biased into their second position by a spring and adjustable to their first position by a lever element 66 against the biasing force.

In the following, the adjustment mechanism of the pins 62 and the second reference surface 58 is described. The second reference surface 58 is defined by a surface of a strip-shaped plate 68 whose first end is equipped with a first arm 70 perpendicular relative to the reference surface 58, this arm being pivotable with respect to an axis 72 (cf. FIG. 2) parallel to reference surface 58. A second arm is mounted to the second end of the strip-shaped plate, this arm being parallel with respect to the first arm and also pivotable about the axis 72. This arm is not shown in the drawings since it extends in a region of the measuring device, that is cut away in FIGS. 2 to 4. The strip-shaped plate 68 and the first and second arms form a U-shaped part.

For adjustment of the second reference surface between its first and its second position, a bar 74 is pivotally mounted with its first end via a joint 76 to a free end of the first arm 70. This bar is also pivotally mounted with its second end via a joint 76 to a first lever 78. This first lever 78 is pivotable about an axis 80 between a first and a second position. This axis 80 is realized by a bolt, which, however, is not shown in FIGS. 3 and 4. In FIG. 4, the first lever 78 is in its first lever position. The lever is biased into this position by means of a spring 82. Upon the lever 78 taking this first lever position, the second reference surface 68 is adjusted via the bar 74 and the first arm 70 into its second position.

The first lever 78 is adjustable from its first into its second position by means of an eccentric drive against the biasing force of the spring 82. The eccentric drive is formed by a rotating disc 84 that is driven by a motor, not shown, and on which a pin 68 is mounted perpendicularly thereto. Upon rotation of the disc in its first rotational direction (cf. FIG. 1 to 4, in a clockwise direction) the pin 86 engages the first lever 78 and moves it into the second lever position, as shown in FIGS. 2 and 3, against the biasing force of the spring 82. Thus, the second reference surface 68 is moved into its first position by means of the bar 74 and the first arm 70.

The lever element 66 is pivotable about an axis 88. This axis 88 is realized by a bolt which is not shown in FIGS. 3 and 4. The spring 82 is fixed to this bolt. In a position of the disc 84, in which the pin 86 holds the second lever 78 in its second lever position against the biasing force of the spring 82, as is the case in FIGS. 2 and 3, the end 90 of the lever element 66 is free so that the springs 64 of the pins 62 relax and take their second position in which they lie completely outside the measuring plane. However, upon rotation of the disc 84 from this position in its second rotational direction (cf. FIG. 1 to 4, in a clockwise direction), the first lever 78 is moved by the spring 82 into its first position, whereby the reference surface 68 moves into its second position. On the other hand, the pin 86 engages the end 90 of the lever element 66 after rotation about a certain angle and pivots the lever element about the axis 88 such that the pins 62 are moved into their second position against the biasing force of the spring 64. This is the position taken during measurement of a test strip, namely in which the second reference surface 68 is turned out of the optical path and the pins 62 protrude into the measuring plane, so that a test strip 12 may be aligned and held by them.

Therefore, by using a single eccentric drive, the adjustment mechanism described facilitates adjustment between a calibration position, in which the second reference surface 68 takes its first position and in which the pins 62 take their second position, and a measuring position, in which the second reference surface 68 takes its second position and the pins 62 take their first position.

The invention claimed is:

1. An optical measuring device for detecting the coloring of test fields of a test strip to be wetted with a liquid for detecting substances in said liquid, whereupon the reflectivity of the test fields changes depending on the concentrations of the substances to be detected, comprising:
   a measuring plane upon which said test strip is to be placed;
   an illumination device for illuminating the measuring plane and the test strip;
   a planar image sensor;
   an optical system for providing an image of the test strip onto said planar image sensor;
   an electronic evaluation unit for evaluating at least one signal generated by said planar image sensor, wherein said illumination device comprises at least two light sources of different colors to alternatively illuminate said test strip in said different colors such that said electronic evaluation unit detects the coloring of said test fields under different color illuminations; and
   an adjustable reference surface that is movable between a first position in which it takes on the position of a test strip during measurement and a second position in which it cannot be imaged by said optical system onto said image sensor.

2. An optical measuring device according to claim 1, wherein said image sensor comprises light sensitive CMOS elements arranged in a planar matrix.

3. An optical measuring device according to claim 1 or 2, wherein said light sources of said illumination device comprise light emitting diodes (LEDs).

4. An optical measuring device according to claim 3, wherein said LEDs comprise blue, green and orange LEDs having approximate wavelengths of 450 nm, 530 nm and 620 nm, respectively.

5. An optical measuring device according to claim 1, wherein said light sources are arranged in a series on a transmitter board.

6. An optical measuring device according to claim 5, wherein the arrangement density of said light sources on the transmitter board increases from near the center of the transmitter board in an outward direction towards the ends of the transmitter board.

7. An optical measuring device according to claims 5 or 6, further comprising a screen on each side of the series of light sources, wherein said screens are disposed in parallel to the longitudinal direction of a test strip so as to focus light reflected from the light sources onto the test strip.

8. An optical measuring device according to claim 7, wherein said screens substantially extend over the length of the series of light sources and comprise a plurality of surface segments extending over the entire length od said screens, wherein said surface segments' inclination angle relative to said transmitter board increases in correspondence with an increasing distance from the transmitter board.

9. An optical measuring device according to claim 7, wherein said screens comprise parts having been milled or manufactured by injection molding, said parts having a reflecting layer or being laminated with a reflecting film.

10. An optical measuring device according to claim 1, further comprising a reference surface, different from the adjustable reference surface, that is disposed such that it is illuminated by said illumination device simultaneously with said test strip and imaged by said optical system onto said image sensor.

11. An optical measuring device according to claim 1, wherein said adjustable reference surface comprises a surface of a strip-shaped plate whose first end is equipped with a first arm substantially perpendicular with respect to said adjustable reference surface, said first arm being pivotable about an axis parallel with respect to said adjustable reference surface.

12. An optical measuring device according to claim 11, further comprising a second arm disposed at a second end of the strip-shaped plate, said second arm being substantially parallel with respect to the first arm and being pivotable about the same axis as the first arm.

13. An optical measuring device according to claims 11 or 12, further comprising a bar pivotally supported by the first arm at the bar's first end for moving the adjustable reference surface from its first to its second position.

14. An optical measuring device according to claim 13, wherein said bar is pivotally secured at its second end to a first lever, said first lever being pivotable about a first lever axis and being biased into a first lever position by means of a biasing element such that said adjustable reference surface takes its second position and wherein said first lever is adjustable to a second lever position against the biasing force of said biasing element such that said adjustable reference surface takes its first position.

15. An optical measuring device according to claim 14, wherein said first lever is actuated by means of an eccentric drive.

16. An optical measuring device according to claim 15, further comprising means for holding and aligning a test strip in its measuring position.

17. An optical measuring device according to claim 16, wherein said means for holding and aligning comprise two substantially parallel pins movable along their longitudinal axis between a first position in which they protrude into said measuring plane and a second position in which they are entirely outside said measuring plane.

18. An optical measuring device according to claim 17, wherein said pins are biased into their second position and being adjustable to their first position against the biasing force by means of a lever element.

19. An optical measuring device according to claim 18, wherein said lever element is adjusted by the same eccentric drive as the first lever.

20. An optical measuring device according to claim 19, wherein said eccentric drive comprises a rotating disc driven by a motor, and a second pin arranged perpendicularly on a surface of said rotating disc such that upon rotation of the disc in a first direction of rotation, said second pin moves said first lever into its second lever position and upon rotation of the disc in a second direction of rotation, said pin moves said lever element such that said lever element moves said substantially parallel pins into their first position.

* * * * *